(12) United States Patent
Zhang et al.

(10) Patent No.: US 7,165,444 B2
(45) Date of Patent: Jan. 23, 2007

(54) CONCENTRATING COLUMN AND SAMPLE PROCESSING DEVICE USEFUL FOR ELEMENTAL ANALYSIS OF TRACE METALS

(75) Inventors: Xinshen Zhang, Chengdu (CN); Xiaoping Jiang, Chengdu (CN)

(73) Assignee: Sichuan University, Sichuan (CN)

( * ) Notice: Subject to any disclaimer, the term of this patent is extended or adjusted under 35 U.S.C. 154(b) by 0 days.

(21) Appl. No.: 11/196,040

(22) Filed: Aug. 3, 2005

(65) Prior Publication Data

US 2006/0039827 A1    Feb. 23, 2006

(30) Foreign Application Priority Data

Aug. 3, 2004    (CN) .................. 2004 1 0040361

(51) Int. Cl.
*G01N 33/00*    (2006.01)
*C02F 1/24*    (2006.01)

(52) U.S. Cl. ................. 73/61.41; 210/692; 95/88
(58) Field of Classification Search ............ 73/23.39, 73/61.53; 210/692; 95/88
See application file for complete search history.

(56) References Cited

U.S. PATENT DOCUMENTS 4,081,401 A * 3/1978 Takegami et al. ........... 502/402
4,081,403 A * 3/1978 Takegami et al. ........... 502/402
4,392,963 A * 7/1983 Perl et al. .................... 210/692

OTHER PUBLICATIONS

Smirnov, I. P. and Nesterenko, P.N. "Use of High-Efficiency Liquid-Chromatography in Determining the Metal Content of Waste-Water", Fibre Chemistry, vol. 24, Sep. 1993, pp. 422-424.*
Pauli, B. and Jones, P. "A Comparative Study of the metal Selective Properties of Chelating dye Impregnated Resins for the Ion Chromatographic Separation of Trace Metals." Chromatographia, vol. 42, May 1996, pp. 528-538.*

* cited by examiner

*Primary Examiner*—Michael Cygan
(74) *Attorney, Agent, or Firm*—Jenkins, Wilson, Taylor & Hunt, P.A.

(57) ABSTRACT

A concentrating column useful for elemental analysis of trace metals consists mainly of column body, filtration membranes 6 fixed at the fluid inlet end and the outlet end of the column body, and column packing 8 packed inside the column body, wherein column packing 8 is prepared from the swollen and cleaned macroporous adsorbent resin of high, medium or non-polarity treated with a mixture of 3 mol/L $NH_4OH$-1 mol/L HAC-3.0~6.0×$10^{-4}$ mol/L pyridin-(2-azo-4-)resorcin or a mixture of 0.5 mol/L $Na_2HPO_4$-1.0~2.0×$10^{-4}$ mol/L pyridin-(2-azo-4-)resorcin by dynamic on-column treatment or static immersion treatment. Two types of sample processing devices useful for elemental analysis of trace metals are provided with concentrating column employing the above-mentioned column packing. The concentrating column of the present invention simplifies the sample processing flow and the structure of sample processing device, saves chemical reagent, increases sample processing rate, and particularly prevents the toxic methanol from doing harm to the operator's health.

15 Claims, 3 Drawing Sheets

US 7,165,444 B2

CONCENTRATING COLUMN AND SAMPLE PROCESSING DEVICE USEFUL FOR ELEMENTAL ANALYSIS OF TRACE METALS

RELATED APPLICATIONS

This application claims the benefit of Chinese Patent Application No. 200410040361.5, filed Aug. 3, 2004; the disclosure of which is incorporated herein by reference in its entirety.

TECHNICAL FIELD

The present invention relates to a concentrating column and sample processing device useful for elemental analysis of trace metals. The concentrating column and sample processing device is especially useful for elemental analysis of trace metals in seawater, river estuary water, and river water.

TECHNICAL BACKGROUND

To provide necessary data and information for studying the relationship between trace metal elements in seawater, river estuary water and river water and ecological environments as well as human activity, elemental analysis of trace amount of metals is needed. The apparatus for analyzing trace metal elements in seawater, river estuary water and river water consists of a sample processing device (separation and enrichment device) and a device for determination of trace metals. A concentrating column is a key component in the sample processing device.

CN application No. 200410021965.5 discloses an autoanalyzer for determination of trace metal elements in seawater and river estuary, the testing device of which is low pressure ion-chromatography, and the operating pressure is $2 \sim 3 \times 10^5$ Pa. Two types of online sample processing devices and three types of concentrating columns are provided. One type of online sample processing device is a direct processing type and comprises a concentrating column, a low pressure pump, a switch valve, a sample container, a washing fluid container and a desorption fluid container, wherein the outlet of a low pressure pump is connected to the fluid inlet of a concentrating column via pipe fittings, the inlet of a low pressure pump is connected to the outlet of a switch valve via pipe fittings, the inlets of a switch valve are connected, via pipe fittings, to a sample container, a washing fluid container and a desorption fluid container respectively. For this type of online sample processing device, the column packing of the concentrating column is an iminodiacetic acid type macroporous adsorption resin or a spherical cellulose adsorbent for metals. The other type of online sample processing device is a complex processing type and comprises a concentrating column, a low pressure pump, a switch valve, a sample container, a washing fluid container, a desorption fluid container, a complexant container and a reactor. There are two low pressure pumps, one is connected between a concentrating column and a switch valve, with its outlet being connected to the inlet of a concentrating column and its inlet to the outlet of a switch valve both via pipe fittings; and the other is connected between the reactor and the sample container as well as a complexant container, with its inlet being connected to a sample container and a complexant container and its outlet to a reactor both via pipe fittings. The inlets of a switch valve are connected, via pipe fittings, to a washing fluid container, a desorption fluid container and a reactor respectively. For this type of online sample processing device, the column packing of the concentrating column is a $C_{18}$ chemically bonded stationary phase.

In analyzing the trace metal elements in seawater and river estuary water, it is known that the column packing of concentrating column generally used is an iminodiacetic acid type macroporous adsorbent resin for high pressure ion chromatography and a $C_{18}$ chemically bonded stationary phase for ICP-emission spectra.

As a packing material for concentrating columns, iminodiacetic acid type macroporous adsorbent resin has the following problems: (1) magnesium and calcium ions have to be removed by ammonium acetate solution and other interfering materials by deionized water before the desorption of trace metals since the magnesium and calcium ions are adsorbed to the concentrating column simultaneously during concentration; (2) there are difficulties during desorption and the desorption fluid used is $0.05 \sim 0.20$ mol/L $HNO_3$ solution which brings undesired effects to the subsequent analysis of trace metal elements.

As a packing material for concentrating columns, a $C_{18}$ chemically bonded stationary phase has the following problems: (1) the processing of samples is so complicated that the trace metals in test samples have to be reacted with a complexant (which is a solution of 8-hydroxyquinoline in ethanol) first to form a metal complex, and then be adsorbed to a concentrating column, after that, deionized water is used as a washing fluid to remove the remaining interfering material in the flow such as sodium chloride, magnesium and calcium, and finally a methanol-water-$HNO_3$ solution is used for desorption, in which a metal complex adsorbed to a concentrating column enters a low pressure ion chromatography system of the device; (2) there is methanol, a toxic material, presents in the desorption fluid, and this is thus harmful to the operator.

Although a spherical cellulose adsorbent for metals does not have the disadvantages of the above-mentioned two packing materials, the process to prepare it is rather complicated.

In addition, the automation extent of the above-mentioned combination of online sample processing device and testing device during analysis is not satisfactory.

DISCLOSURE OF THE INVENTION

An object of the invention is to overcome the disadvantages of the prior art and to provide a concentrating column with better adsorption effect and that is easier to prepare and a sample processing device combined more reasonably with the testing device, for better elemental analysis of trace metals in seawater, river estuary water, and river water.

The concentrating column of the present invention comprises a column body, a filtration membranes fixed at the fluid inlet end and the outlet end of the column body, and a column packing packed inside the column body. The column packing is prepared from a swollen and cleaned macroporous adsorbent resin of high, medium or non-polarity treated with a mixture of 3 mol/L $NH_4OH$-1 mol/L HAC-$3.0 \sim 6.0 \times 10^{-4}$ mol/L pyridin-(2-azo-4-)resorcin or a mixture of 0.5 mol/L $Na_2HPO_4$-$1.0 \sim 2.0 \times 10^{-4}$ mol/L pyridin-(2-azo-4-)resorcin by dynamic on-column treatment or static immersion treatment.

Swelling of the macroporous adsorbent resin of high, medium or non-polarity is carried out by immersion in ethanol under room temperature for at least 8 hours. The cleansing of the macroporous adsorbent resin of high, medium or non-polarity is carried out by washing the swollen resin with deionized water.

The dynamic on-column treatment of the swollen and cleaned macroporous adsorbent resin of high, medium or non-polarity with a mixture of $NH_4OH$-HAC-pyridin-(2-azo-4-) resorcin is carried out by packing the swollen and cleaned macroporous adsorbent resin of high, medium or non-polarity into a column, pumping the formulated mixture of 3 mol/L $NH_4OH$-1 mol/L HAC-$3.0\sim6.0\times10^{-4}$ mol/L pyridin-(2-azo-4-) resorcin into the concentrating column directly or after being diluted 2–4 times with deionized water until the effluent turns from colorless to orange, and washing the concentrating column by pumping deionized water through the column until the effluent turns from orange to colorless. The dynamic on-column treatment of the swollen and cleaned macroporous adsorbent resin of high, medium or non-polarity with a mixture of $Na_2HPO_4$-pyridin-(2-azo-4-)resorcin is carried out by packing the swollen and cleaned macroporous adsorbent resin of high, medium or non-polarity into column, pumping the formulated mixture of 0.5 mol/L $Na_2HPO_4$-$1.0\sim2.0\times10^{-4}$ mol/L pyridin-(2-azo-4-)resorcin through the concentrating column until the effluent turns from colorless to orange red, and washing the concentrating column by pumping deionized water through the column until the effluent turns from orange red to colorless.

The static immersion treatment of the swollen and cleaned macroporous adsorbent resin of high, medium or non-polarity with a mixture of $NH_4OH$-HAC-pyridin-(2-azo-4-) resorcin or $Na_2HPO_4$-pyridin-(2-azo-4-)resorcin is carried out by immersing the swollen and cleaned macroporous adsorbent resin of high, medium or non-polarity in the formulated mixture of 3 mol/L $NH_4OH$-1 mol/L HAC-$3.0\sim6.0\times10^{-4}$ mol/L pyridin-(2-azo-4-) resorcin or 0.5 mol/L $Na_2HPO_4$-$1.0\sim2.0\times10^{-4}$ mol/L pyridin-(2-azo-4-)resorcin under room temperature for at least 30 minutes, and after immersion washing it with deionized water until the washing fluid turns colorless.

A suitable macroporous adsorbent resin of high, medium or non-polarity is commercially available or can be prepared from styrene, divinylbenzene and pore-forming agent (e.g. toluene).

The sample processing device useful for analysis of trace metals of the present invention can be divided into two types:

The first type comprises a concentrating column, a low pressure pump, a switch valve, a washing fluid container, a sample container, a desorption fluid container, a six-way automatic sampling valve and a transporting pump. The aforementioned components should be assembled so that the inlet of the transporting pump is connected to the desorption fluid container via pipe fittings, the outlet of the transporting pump is connected to one fluid inlet of the six-way automatic sampling valve via pipe fittings, the outlet of the low pressure pump is connected to one fluid inlet of the six-way automatic sampling valve via pipe fittings, the inlet of the low pressure pump is connected to the outlet of the switch valve via pipe fittings, the inlets of the switch valve are connected via pipe fittings to the sample container and the washing fluid container respectively, the fluid inlet and outlet of concentrating column are connected via pipe fittings to the fluid outlet and inlet of the six-way automatic sampling valve respectively, and one fluid outlet of the six-way automatic sampling valve is connected to the corresponding component of the testing device via pipe fittings.

The other type comprises a concentrating column, a low pressure pump, a switch valve, a washing fluid container, a sample container and a desorption fluid container. The aforementioned components are assembled so that the fluid outlet of the concentrating column is connected to the corresponding component of the testing device via pipe fittings, the outlet of the low pressure pump is connected to the fluid inlet of the concentrating column via pipe fittings, the inlet of the low pressure pump is connected to the outlet of the switch valve via pipe fittings, the inlets of the switch valve are connected via pipe fittings to the sample container, the washing fluid container and the desorption container respectively.

The concentrating columns of the previously described two types of sample processing device both comprise a column body, a filtration membranes fixed at the fluid inlet end and outlet end of the column body, and the column packing packed inside the column body, wherein the column packing is prepared from the swollen and cleaned macroporous adsorbent resin of high, medium or non-polarity treated with a mixture of 3 mol/L $NH_4OH$-1 mol/L HAC-$3.0\sim6.0\times10^{-4}$ mol/L pyridin-(2-azo-4-)resorcin or a mixture of 0.5 mol/L $Na_2HPO_4$-$1.0\sim2.0\times10^{-4}$ mol/L pyridin-(2-azo-4-)resorcin by dynamic on-column treatment or static immersion treatment.

The concentrating column and the sample processing device of the present invention can be used in combination with low pressure ion chromatography, high pressure ion chromatography and an ICP analyzer for analysis of trace metals element in seawater, river estuary water and river water.

The present invention provides the following advantages:

1. The column packing of the concentrating column, which is prepared from the swollen and cleaned macroporous adsorbent resin of high, medium or non-polarity treated with a mixture of 3 mol/L $NH_4OH$-1 mol/L HAC-$3.0\sim6.0\times10^{-4}$ mol/L pyridin-(2-azo-4-) resorcin by dynamic on-column treatment, does not need test samples to be processed by complexation, has a sampling flow rate up to 4 ml/min during concentration without any adsorption of magnesium or calcium ion, is able to work properly with $5\sim8\times10^{-3}$ mol/L $HNO_3$ solution during the course of desorption, and therefore simplifies the sample processing flow and the structure of sample processing device, saves chemical reagent, increases the sample processing rate, and particularly prevents the toxic methanol from doing harm to the operator's health.

2. The column packing of the concentrating column which is prepared from the swollen and cleaned macroporous adsorbent resin of high, medium or non-polarity treated with a mixture of 0.5 mol/L $Na_2HPO_4$-$1.0\sim2.0\times10^{-4}$ mol/L pyridin-(2-azo-4-)resorcin by dynamic on-column treatment has, in addition to the simplification of sample processing flow and the structure of sample processing device, saving of chemical reagent and the increasing of sample processing rate, the advantages of being able to adsorb $Hg^{2+}$ in the sample to concentrating column and thus being useful for analyzing $Hg^{2+}$ in seawater, river estuary water and river water.

3. It is simple to prepare the column packing of the concentrating column and thus contributes to reduction of cost.

4. The sample processing device is particularly useful for online analysis of trace metals in seawater, river estuary water and river water.

Figure 1:
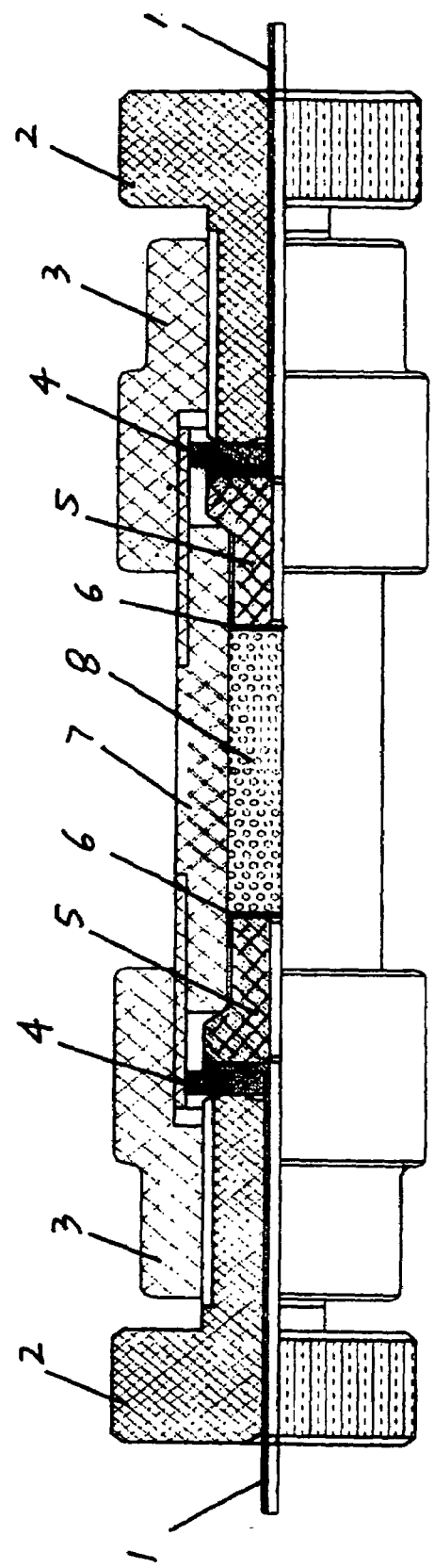
FIG. 1 is a structural diagram of the concentrating column for analyzing trace metal elements according to the present invention.

In the drawings, the numerals represent: 1-conduit, 2-conduit-holding bolt, 3-connection cannula, 4-sealing ring, 5-plug, 6-filtration membrane, 7-column tube, 8-column packing, 9-six-way automatic sampling valve, 10-concentrating column, 11-low pressure pump, 12-switch valve, 13-washing fluid container, 14-sample container, 15-desorption fluid container, 16-transporting pump, 17-testing device.

DETAILED DESCRIPTION OF THE INVENTION

It is to be noted that the term "a" or "an" entity refers to one or more of that entity.

The following examples are provided for illustrative purposes only and are not intended to limit the scope of the invention.

EXAMPLE 1

The Column Packing of the Concentrating Column is Prepared by Treating a Non-Polar Macroporous Adsorbent Resin The concentrating column of Example 1 has a structure as shown in FIG. 1, it consists mainly of column body, filtration membranes (6) and column packing (8); column body is made of nylon and comprises column tube (7), plugs (5) at both ends of the inside of column tube, conduit-holding bolts (2) putting pressure on the plugs, and connection cannulas (3) connecting column tube and conduit-holding bolts. Conduits (1) were fixed in the central holes of conduit-holding bolts (2), the insertion ends of conduits (1) have discs in close contact with the plugs, the sealing rings (4) lie between the discs and the end surface of conduit-holding bolts, conduits (1) were connected to the central holes of plugs (5) to form a channel for fluid input and output; filtration membranes (6) were made of nylon taffeta and were fixed respectively at the end surface of the insertion sections of the plugs at both ends of the inside of column tube; column packing (8), prepared with non-polar macroporous adsorbent resin Amberlite XAD-1~Amberlite XAD-5 available from Rohm & Hass Co., USA and D3520 available from Nankai University, Tianjin China, were packed into the inside of column tube according to the following procedures:

1. Immersion swelling and cleansing

The above-mentioned non-polar macroporous adsorbent resin was added to the ethanol containing container, and was immersed in it at 25° C. After 8 hours when the resin was adequately swollen, it was washed with deionized water until it was ethanol free.

2. Dynamic on-column treatment with a mixture of $NH_4OH$-HAC-pyridin-(2-azo-4-) resorcin 1) Preparation of the mixture For future use, the four kinds of mixture shown in Tab. 1 were prepared using $NH_4OH$, HAC, pyridine-(2-azo-4-) resorcin (PAR), and deionized water.

2) Packing of the concentrating column

The non-polar macroporous adsorbent resin after immersion swelling and cleansing was added to the inside of column tube of the column body via a dropper, and was washed with deionized water.

3) On-column treatment

TABLE 1

| Mixture Concentration | Undiluted or Dilution Times | Flow Rate (ml/min) |
|---|---|---|
| 3 mol/L $NH_4OH$ - 1 mol/L HAC - $3.0 \times 10^{-4}$ mol/L pyridin-(2-azo-4-) resorcin | 2 times | 1 |
| 3 mol/L $NH_4OH$ - 1 mol/L HAC - $4.0 \times 10^{-4}$ mol/L pyridin-(2-azo-4-) resorcin | Undiluted | 1 |
| 3 mol/L $NH_4OH$ - 1 mol/L HAC - $5.0 \times 10^{-4}$ mol/L pyridin-(2-azo-4-) resorcin | 3 times | 1.5 |
| 3 mol/L $NH_4OH$ - 1 mol/L HAC - $6.0 \times 10^{-4}$ mol/L pyridin-(2-azo-4-) resorcin | 4 times | 2 |

The formulated mixture of $NH_4OH$-HAC-pyridin-(2-azo-4-) resorcin undiluted or diluted with deionized water according to Table 1 was pumped into the concentrating column at the flow rates shown in Table 1 until the effluent turns from colorless to orange. Then deionized water was pumped through to wash the concentrating column until the effluent turns from orange to colorless. And thus, the concentrating column for treating samples was prepared.

3. Dynamic on-column treatment with the mixture of $Na_2HPO_4$-pyridin-(2-azo-4-) resorcin 1) Preparation of the mixture For future use, the three kinds of mixture shown in Table 2 were prepared by dissolving $Na_2HPO_4 \cdot 12H_2O$ into deionized water and adding thereto pyridine-(2-azo-4-) resorcin (PAR).

2) Packing of the concentrating column

The non-polar macroporous adsorbent resin after immersion swelling and cleansing was added to the inside of column tube of the column body via dropper, and was washed with deionized water.

3) On-column treatment

TABLE 2

| Mixture Concentration | Flow rate (ml/min) |
|---|---|
| 0.5 mol/L $Na_2HPO_4$ - $1.0 \times 10^{-4}$ mol/L pyridin-(2-azo-4-) resorcin | 1 |
| 0.5 mol/L $Na_2HPO_4$ - $1.5 \times 10^{-4}$ mol/L pyridin-(2-azo-4-) resorcin | 0.8 |
| 0.5 mol/L $Na_2HPO_4$ - $2.0 \times 10^{-4}$ mol/L pyridin-(2-azo-4-) resorcin | 0.5 |

The formulated mixture of $Na_2HPO_4$-pyridin-(2-azo-4-) resorcin was pumped into the concentrating column at the flow rates shown in Table 2 until the effluent turns from colorless to orange red. Then deionized water was pumped through to wash the concentrating column until the effluent turns from orange red to colorless. And thus, the concentrating column for treating samples was prepared.

4. Static immersion treatment with $NH_4OH$-HAC-pyridin-(2-azo-4-) resorcin mixture

TABLE 3

| Mixture Concentraion | Immersion Temperature (° C.) | Immersion Time (min) |
|---|---|---|
| 3 mol/L $NH_4OH$ - 1 mol/L HAC - 3.0 × $10^{-4}$ mol/L pyridin-(2-azo-4-) resorcin | 25 | 40 |
| 3 mol/L $NH_4OH$ - 1 mol/L HAC - 4.0 × $10^{-4}$ mol/L pyridin-(2-azo-4-) resorcin | 25 | 40 |
| 3 mol/L $NH_4OH$ - 1 mol/L HAC - 5.0 × $10^{-4}$ mol/L pyridin-(2-azo-4-) resorcin | 25 | 30 |
| 3 mol/L $NH_4OH$ - 1 mol/L HAC - 6.0 × $10^{-4}$ mol/L pyridin-(2-azo-4-) resorcin | 25 | 30 |

The four kinds of mixture shown in Table 3 were prepared with $NH_4OH$, HAC and pyridin-(2-azo-4-)resorcin. The non-polar macroporous adsorbent resin after immersion swelling and cleansing was immersed in a container containing the mixture for the period of time and temperature shown in Table 3. After immersion, the resin was washed with deionized water until the washing fluid turned colorless. Then the macroporous adsorbent resin after static immersion and washing was added to the inside of column tube of the column body via a dropper, and thus the concentrating column for treating samples was prepared.

5. Static immersion treatment with $Na_2HPO_4$-pyridin-(2-azo-4-)resorcin mixture

TABLE 4

| Mixture Concentration | Immersion Temperature (° C.) | Immersion Time (min) |
|---|---|---|
| 0.5 mol/L $Na_2HPO_4$ - 1.0 × $10^{-4}$ mol/L pyridin-(2-azo-4-)resorcin | 25 | 40 |
| 0.5 mol/L $Na_2HPO_4$ - 1.5 × $10^{-4}$ mol/L pyridin-(2-azo-4-)resorcin | 25 | 35 |
| 0.5 mol/L $Na_2HPO_4$ - 2.0 × $10^{-4}$ mol/L pyridin-(2-azo-4-)resorcin | 25 | 30 |

To prepare the mixture shown in Table 4, $Na_2HPO_4 \cdot 12H_2O$ was dissolved in deionized water, and pyridin-(2-azo-4)resorcin was then added thereto. The non-polar macroporous adsorbent resin after immersion swelling and cleansing was immersed in a container containing the mixture for the period of time and temperature shown in Table 4. After immersion, the resin was washed with deionized water until the washing fluid turned colorless. Then the macroporous adsorbent resin after static immersion and washing was added to the inside of column tube of the column body via a dropper, and thus the concentrating column for treating samples was prepared.

EXAMPLE 2

The Packing Material of the Concentrating Column is Prepared by Treating a Macroporous Adsorbent Resin of Medium Polarity As shown in FIG. 1, the structure of the concentrating column in Example 2 was the same as that in Example 1. However, the difference between them is that in Example 2 the column packing (8) was prepared with macroporous adsorbent resin of medium polarity such as Amberlite XAD-6, Amberlite XAD-7 and Amberlite XAD-8, available from Rohm & Hass Co., USA according to the following procedures:

1. Immersion swelling and cleansing

The above-mentioned medium polar macroporous adsorbent resin was added to an ethanol containing container, and was immersed in it at 25° C. After 8 hours when the resin was adequately swollen, it was washed with deionized water until it was ethanol free.

2. Dynamic on-column treatment with the mixture of $NH_4OH$-HAC-pyridin-(2-azo-4-) resorcin 1) Preparation of the mixture For future use, the four kinds of mixture shown in Table 5 were prepared using $NH_4OH$, HAC, pyridine-(2-azo-4-) resorcin (PAR), and deionized water.

2) Packing of the concentrating column

The medium polar macroporous adsorbent resin after immersion swelling and cleansing was added into the inside of column tube of column body via dropper, and was washed with deionized water.

3) On-column treatment

TABLE 5

| Mixture Concentration | Undiluted or Dilution Times | Flow Rate (ml/min) |
|---|---|---|
| 3 mol/L $NH_4OH$ - 1 mol/L HAC - 3.0 × $10^{-4}$ mol/L pyridine-(2-azo-4-) resorcin | Undiluted | 1 |
| 3 mol/L $NH_4OH$ - 1 mol/L HAC - 4.0 × $10^{-4}$ mol/L pyridine-(2-azo-4-) resorcin | 2 times | 1.5 |
| 3 mol/L $NH_4OH$ - 1 mol/L HAC - 5.0 × $10^{-4}$ mol/L pyridine-(2-azo-4-) resorcin | Undiluted | 0.6 |
| 3 mol/L $NH_4OH$ - 1 mol/L HAC - 6.0 × $10^{-4}$ mol/L pyridine-(2-azo-4-) resorcin | 4 times | 2 |

The formulated mixture of $NH_4OH$-HAC-pyridin-(2-azo-4-)resorcin undiluted or diluted with deionized water according to Table 5 was pumped into the concentrating column at the flow rates shown in Table 5 until the effluent turns from colorless to orange. Then deionized water was pumped through to wash the concentrating column until the effluent turns from orange to colorless. And thus, the concentrating column for treating samples was prepared.

3. Dynamic on-column treatment with the mixture of $Na_2HPO_4$-pyridin-(2-azo-4-) resorcin 1) Preparation of the mixture For future use, the three kinds of mixture shown in Table 6 were prepared by dissolving $Na_2HPO_4 \cdot 12H_2O$ into deionized water and adding thereto pyridin-(2-azo-4-) resorcin (PAR).

2) Packing of the concentrating column

The medium polar macroporous adsorbent resin after immersion swelling and cleansing was added to the inside of column tube of column body via a dropper, and was washed with deionized water.

3) On-column treatment

TABLE 6

| Mixture Concentration | Flow rate (ml/min) |
|---|---|
| 0.5 mol/L $Na_2HPO_4$ - 1.0 × $10^{-4}$ mol/L pyridine-(2-azo-4-) resorcin | 1 |
| 0.5 mol/L $Na_2HPO_4$ - 1.5 × $10^{-4}$ mol/L pyridine-(2-azo-4-) resorcin | 0.8 |
| 0.5 mol/L $Na_2HPO_4$ - 2.0 × $10^{-4}$ mol/L pyridine-(2-azo-4-) resorcin | 0.5 |

The formulated mixture of $Na_2HPO_4$-pyridin-(2-azo-4-) resorcin was pumped through the concentrating column at the flow rates shown in Table 6 until the effluent turned from colorless to orange red. Then deionized water was pumped through to wash the concentrating column until the effluent turned from orange red into colorless. And thus, the concentrating column for treating samples was prepared.

4. Static immersion treatment with $NH_4OH$-HAC-pyridin-(2-azo-4-) resorcin mixture

TABLE 7

| Mixture Concentration | Immersion Temperature (° C.) | Immersion Time (min) |
|---|---|---|
| 3 mol/L $NH_4OH$ - 1 mol/L HAC - $3.0 \times 10^{-4}$ mol/L pyridine-(2-azo-4-) resorcin | 25 | 40 |
| 3 mol/L $NH_4OH$ - 1 mol/L HAC - $4.0 \times 10^{-4}$ mol/L pyridine-(2-azo-4-) resorcin | 25 | 40 |
| 3 mol/L $NH_4OH$ - 1 mol/L HAC - $5.0 \times 10^{-4}$ mol/L pyridine-(2-azo-4-) resorcin | 25 | 30 |
| 3 mol/L $NH_4OH$ - 1 mol/L HAC - $6.0 \times 10^{-4}$ mol/L pyridine-(2-azo-4-) resorcin | 25 | 30 |

The four kinds of mixture shown in Table 7 were prepared with $NH_4OH$, HAC, pyridin-(2-azo-4-) resorcin. The medium polar macroporous adsorbent resin after immersion swelling and cleansing was immersed in a container containing the mixture for the period of time and temperature shown in Table 7. After immersion, the resin was washed with deionized water until the washing fluid turned colorless. Then the macroporous adsorbent resin after static immersion and washing was added to the inside of column tube of the column body via a dropper, and thus the concentrating column for treating samples was prepared.

5. Static immersion treatment with $Na_2HPO_4$-pyridin-(2-azo-4-)resorcin mixture

TABLE 8

| Mixture Concentration | Immersion Temperature (° C.) | Immersion Time (min) |
|---|---|---|
| 0.5 mol/L $Na_2HPO_4$ - $1.0 \times 10^{-4}$ mol/L pyridine-(2-azo-4-) resorcin | 25 | 40 |
| 0.5 mol/L $Na_2HPO_4$ - $1.5 \times 10^{-4}$ mol/L pyridine-(2-azo-4-) resorcin | 25 | 35 |
| 0.5 mol/L $Na_2HPO_4$ - $2.0 \times 10^{-4}$ mol/L pyridine-(2-azo-4-) resorcin | 25 | 30 |

The three kinds of mixture shown in Table 8 were prepared by dissolving $Na_2HPO_4 \cdot 12H_2O$ into deionized water and adding thereto pyridin-(2-azo-4-) resorcin. The medium polar macroporous adsorbent resin after immersion swelling and cleansing was then immersed in a container containing said mixture for the period of time and temperature both shown in Table 8. After immersion completes, the resin was washed with deionized water until the washing fluid turned colorless. Then the macroporous adsorbent resin after static immersion and washing was added to the inside of column tube of the column body via a dropper, and thus the concentrating column for treating samples was prepared.

EXAMPLE 3

The Packing Material of the Concentrating Column is Prepared by Treating Macroporous Adsorbent Resin of High Polarity As shown in FIG. 1, the structure of the concentrating column in Example 3 was the same as that in Example 1. However, the difference between them was that in this Example column packing 8 was prepared with highly polar macroporous adsorbent resin, Amberlite XAD-9 and Amberlite XAD-10 available from Rohm & Hass Co,. USA and NKA available from NanKai University, TianJin China, according to the following procedures:

1. Immersion swelling and cleansing

The above-mentioned high-polar macroporous adsorbent resin was added to the ethanol containing container, and was immersed in it at 25° C. After 8 hours when the resin was adequately swollen, it was washed with deionized water until it was ethanol free.

2. Dynamic on-column treatment with the mixture of $NH_4OH$-HAC-pyridin-(2-azo-4-) resorcin 1) Preparation of the mixture For future use, the four kinds of mixture shown in Table 9 were prepared using $NH_4OH$, HAC, pyridin-(2-azo-4-) resorcin(PAR), and deionized water.

2) Packing of the concentrating column

The high-polar macroporous adsorbent resin after immersion swelling and cleansing was added into the inside of column tube of the column body via a dropper, and was washed with deionized water.

3) On-column treatment

TABLE 9

| Mixture Concentration | Undiluted or Dilution Times | Flow Rate (ml/min) |
|---|---|---|
| 3 mol/L $NH_4OH$ - 1 mol/L HAC - $3.0 \times 10^{-4}$ mol/L pyridin-(2-azo-4-) resorcin | Undiluted | 1 |
| 3 mol/L $NH_4OH$ - 1 mol/L HAC - $4.0 \times 10^{-4}$ mol/L pyridin-(2-azo-4-) resorcin | 2 times | 1.5 |
| 3 mol/L $NH_4OH$ - 1 mol/L HAC - $5.0 \times 10^{-4}$ mol/L pyridin-(2-azo-4-) resorcin | 3 times | 1.5 |
| 3 mol/L $NH_4OH$ - 1 mol/L HAC - $6.0 \times 10^{-4}$ mol/L pyridin-(2-azo-4-) resorcin | Undiluted | 0.5 |

The formulated mixture of $NH_4OH$-HAC-pyridin-(2-azo-4-) resorcin undiluted or diluted with deionized water according to Table 9 was pumped through the concentrating column at the flow rates shown in Table 9 until the effluent turned from colorless to orange. Then deionized water was pumped through to wash the concentrating column until the effluent turned from orange to colorless. And thus, the concentrating column for treating samples was prepared.

3. Dynamic on-column treatment with the mixture of $Na_2HPO_4$-pyridin-(2-azo-4-) resorcin 1) Preparation of the mixture For future use, the three kinds of mixture shown in Table 2 were prepared by dissolving $Na_2HPO_4 \cdot 12H_2O$ into deionized water and adding thereto pyridin-(2-azo-4-) resorcin (PAR).

2) Packing of the concentrating column

The high polar macroporous adsorbent resin after immersion swelling and cleansing was added into the inside of column tube of column body via dropper, and was washed with deionized water.

3) On-column treatment

TABLE 10

| Mixture Concentration | Flow rate (ml/min) |
|---|---|
| 0.5 mol/L $Na_2HPO_4$ - $1.0 \times 10^{-4}$ mol/L pyridine-(2-azo-4-) resorcin | 1 |

TABLE 10-continued

| Mixture Concentration | Flow rate (ml/min) |
|---|---|
| 0.5 mol/L $Na_2HPO_4$ - $1.5 \times 10^{-4}$ mol/L pyridine-(2-azo-4-) resorcin | 0.8 |
| 0.5 mol/L $Na_2HPO_4$ - $2.0 \times 10^{-4}$ mol/L pyridine-(2-azo-4-) resorcin | 0.5 |

The formulated mixture of $Na_2HPO_4$-pyridin-(2-azo-4-) resorcin was pumped through the concentrating column at the flow rates shown in Table 10 until the effluent turns from colorless to orange red. Then deionized water was then pumped through to wash the concentrating column until the effluent turns from orange red to colorless. And thus, the concentrating column for treating samples was prepared.

4. Static immersion treatment with $NH_4OH$-HAC-pyridin-(2-azo-4-) resorcin mixture

TABLE 11

| Mixture Concentraion | Immersion Temperature (° C.) | Immersion Time (min) |
|---|---|---|
| 3 mol/L $NH_4OH$ - 1 mol/L HAC - $3.0 \times 10^{-4}$ mol/L pyridine-(2-azo-4-) resorcin | 25 | 40 |
| 3 mol/L $NH_4OH$ - 1 mol/L HAC - $4.0 \times 10^{-4}$ mol/L pyridine-(2-azo-4-) resorcin | 25 | 40 |
| 3 mol/L $NH_4OH$ - 1 mol/L HAC - $5.0 \times 10^{-4}$ mol/L pyridine-(2-azo-4-) resorcin | 25 | 30 |
| 3 mol/L $NH_4OH$ - 1 mol/L HAC - $6.0 \times 10^{-4}$ mol/L pyridine-(2-azo-4-) resorcin | 25 | 30 |

The four kinds of mixture shown in Table 11 were prepared with $NH_4OH$, HAC, pyridin-(2-azo-4-) resorcin. The high-polar macroporous adsorbent resin after immersion swelling and cleansing was immersed in a container containing the mixture for the period of time and temperature shown in Table 11. After immersion, the resin was washed with deionized water until the washing fluid turned colorless. Then the macroporous adsorbent resin after static immersion and washing was added to the inside of column tube of the column body via a dropper, and thus the concentrating column for treating samples was prepared.

5. Static immersion treatment with $Na_2HPO_4$-pyridin-(2-azo-4-)resorcin mixture

TABLE 12

| Mixture Concentration | Immersion Temperature (° C.) | Immersion Time (min) |
|---|---|---|
| 0.5 mol/L $Na_2HPO_4$ - $1.0 \times 10^{-4}$ mol/L pyridine-(2-azo-4-) resorcin | 25 | 40 |
| 0.5 mol/L $Na_2HPO_4$ - $1.5 \times 10^{-4}$ mol/L pyridine-(2-azo-4-) resorcin | 25 | 35 |
| 0.5 mol/L $Na_2HPO_4$ - $2.0 \times 10^{-4}$ mol/L pyridine-(2-azo-4-) resorcin | 25 | 30 |

The three kinds of mixture shown in Table 12 were prepared by dissolving $Na_2HPO_4 \cdot 12H_2O$ into deionized water and adding pyridin-(2-azo-4-) resorcin thereto. The high polar macroporous adsorbent resin after immersion swelling and cleansing was immersed in a container containing said mixture for the period of time and temperature shown in Table 12. After immersion, the resin was washed with deionized water until the washing fluid turned colorless. Then the macroporous adsorbent resin after static immersion and washing was added into the inside of column tube of the column body via a dropper, and thus the concentrating column for treating samples was prepared.

EXAMPLE 4

Figure 2:
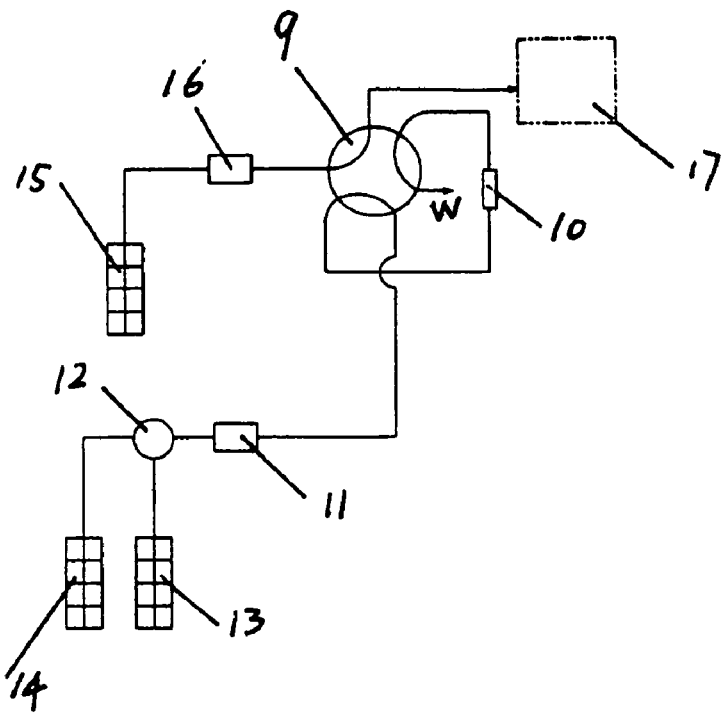
FIG. 2 is a structural diagram of the sample processing device for analyzing trace metal elements according to the present invention, wherein the sample processing device is in sample concentrating mode.
Figure 3:
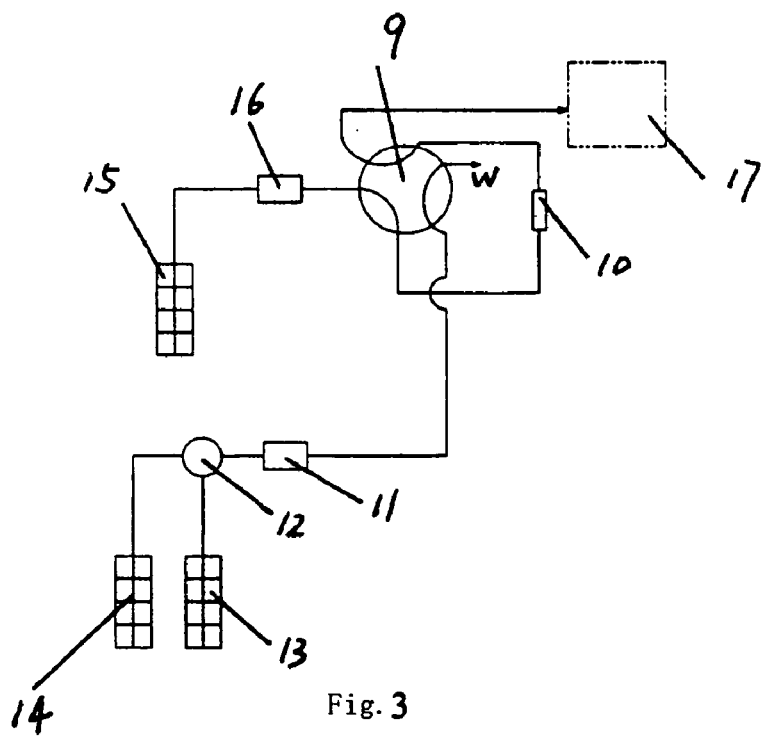
FIG. 3 is a diagram of the sample processing device of FIG. 2 in sample desorbing mode.

The structure of the sample processing device of the present Example is shown in FIG. 2 and FIG. 3. It comprises a six-way automatic sampling valve 9, a concentrating column 10, a low pressure pump 11, a switch valve 12, a washing fluid container 13, a sample container 14, a desorption fluid container 15, and a transporting pump 16. The six-way automatic sampling valve 9 has a structure proposed in CN Pat. No. ZL 02244841.1. The cross-sectional diameter of concentrating column 10 $\phi$=5 mm, and the length is 80 mm, column packing 8 is prepared with the materials and by the method set forth in Example 1, 2 or 3. Low pressure pump 11 is a commercially available electrical peristaltic pump (also known as electrical micropump), and its maximum pressure output is $0 \sim 5 \times 10^5$ Pa. The operating pressure of the transporting pump 16 matches that of the corresponding testing device. The aforementioned components were assembled so that the inlet of transporting pump 16 was connected to the desorption fluid container 15 via pipe fittings, the outlet of the transporting pump 16 was connected to one fluid inlet of the six-way valve 9 via pipe fittings, the outlet of the low pressure pump 11 was connected to one fluid inlet of the six-way automatic sampling valve 9 via pipe fittings, the inlet of the low pressure pump 11 was connected to the outlet of switch valve 12 via pipe fittings, the inlets of the switch valve 12 were connected to the sample container 14 and the washing fluid container 13 respectively via pipe fittings, the fluid inlet and outlet of the concentrating column 10 were connected to the fluid outlet and inlet of the six-way valve 9 respectively via pipe fittings, one fluid outlet of the six-way valve 9 was connected to the corresponding component of testing device 17 via pipe fittings.

Washing fluid: deionized water
Desorption fluid: $5 \sim 8 \times 10^4$ mol/L $HNO_3$ solution
Concentrating flow rate: 3~4 ml/min Work flow: 1. The device was operated to allow the sample processing device to work in a mode as shown in FIG. 2 so that the low pressure 11 may pump the test seawater, river estuary water or river water into the concentrating column 10, allowing the trace metals in test samples to be adsorbed to the concentrating column 10, and the remaining interfering material in the related flow to be removed by pumping deionized water as washing fluid into the concentrating column with a low pressure pump 11; 2. The device was operated to allow the sample processing device to work in a mode as shown in FIG. 3, in which the desorption fluid $HNO_3$ solution was pumped into a concentrating column 10 with a transporting pump 16 so that the trace metal elements adsorbed to the concentrating column were desorbed and flowed through the six-way automatic sampling valve 9 to be tested in the testing device 17, and thus chromatograms of trace metal elements such as $Cu^{2+}$, $Ni^{2+}$, $Zn^{2+}$, $Pb^{2+}$, $Cd^{2+}$ and the like were obtained.

EXAMPLE 5

Figure 4:
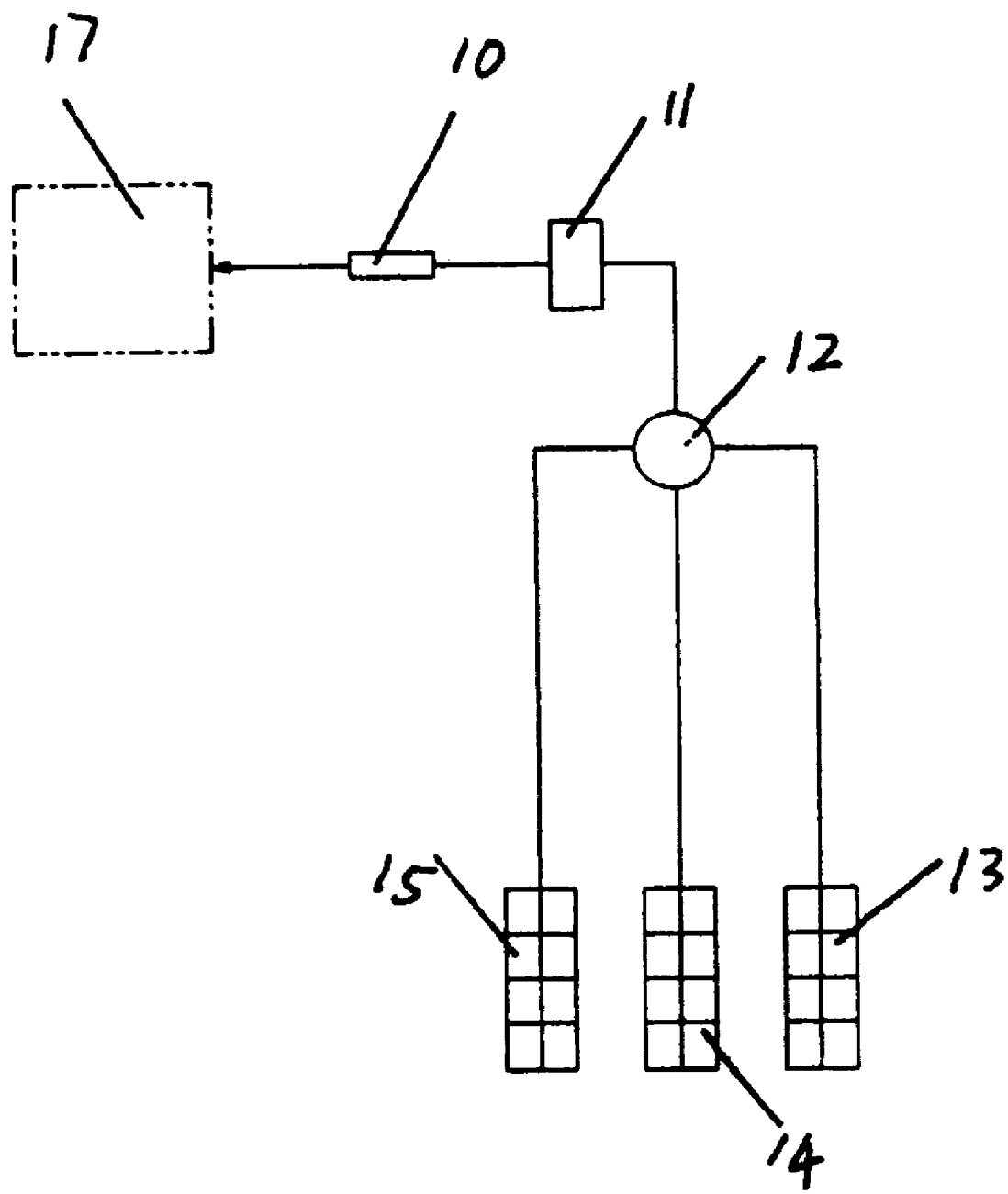
FIG. 4 is another structural diagram of the sample processing device for analyzing trace metals according to the present invention.

The structure of sample processing device of the present Example is shown in FIG. 4, it comprises a concentrating column 10, a low pressure pump 11, a switch valve 12, a washing fluid container 13, a sample container 14, and a desorption fluid container 15. The cross-sectional diameter of concentrating column 10 $\phi$=5 mm, and the length is 80 mm, column packing 8 is prepared with the materials and by the method set forth in Example 1, 2 or 3. Low pressure pump 11 is a commercially available electrical peristaltic pump (also known as electrical micropump), and the maximum pressure output was 0~5×10$^5$ Pa. The aforementioned components were assembled so that the outlet of concentrating column 10 was connected to the corresponding component of the testing device 17 via pipe fittings, the outlet of the low pressure pump 11 was connected to the fluid inlet of the concentrating column 10 via pipe fittings, the inlet of the low pressure pump 11 was connected to the outlet of the switch valve 12 via pipe fittings, the inlets of the switch valve 12 were connected via pipe fittings to the sample container 14, the washing fluid container 13 and the desorption fluid container 15 respectively.

Washing fluid: deionized water
Desorption fluid: 5~8×10$^{-4}$ mol/L HNO$_3$ solution
Concentrating flow rate: 3~4 ml/min Work flow: 1. The device was operated to pump the test seawater, river estuary water or river water into the concentrating column 10 with the low pressure pump 11, allowing the trace metals in the test samples to be adsorbed to the concentrating column 10; 2. Deionized water was pumped as washing fluid into the concentrating column 10 with the low pressure pump 11 to remove the remaining interfering material in the concentrating column; 3. HNO$_3$ solution is pumped as desorption fluid into the concentrating column 10 with the low pressure pump 11 so that the trace metal elements adsorbed to the concentrating column 10 was desorbed and flowed through the sampling valve to be tested in the testing device 17, and thus chromatograms of trace metal elements such as Hg$^{2+}$, Cu$^{2+}$, Zn$^{2+}$ and the like were obtained.

While the invention has been shown and described with reference to a certain preferred embodiment thereof, it will be understood by those skilled in the art that various changes in form and details may be made therein without departing from the spirit and scope of the invention as defined by the appended claims.

We claim:

1. A concentrating column useful for elemental analysis of trace metals, comprising a column body, filtration membranes fixed at the fluid inlet end and the outlet end of the column body, and column packing packed inside the column body, the column packing is prepared from a swollen and cleaned macroporous adsorbent resin of high, medium or non-polarity treated with a mixture of 3 mol/L NH$_4$OH-1 mol/L HAC-3.0~6.0×10$^{-4}$ mol/L pyridin-(2-azo-4-)resorcin or a mixture of 0.5 mol/L Na$_2$HPO$_4$-1.0~2.0×10$^{-4}$ mol/L pyridin-(2-azo-4-)resorcin.

2. The concentrating column of claim 1, wherein the swollen and cleaned macroporous adsorbent resin of high, medium or non-polarity is treated by dynamic on-column treatment.

3. The concentrating column of claim 1, wherein the swollen and cleaned macroporous adsorbent resin of high, medium or non-polarity is treated by static immersion treatment.

4. The concentrating column of claim 1, wherein the swelling of the macroporous adsorbent resin of high, medium or non-polarity is carried out by immersion in ethanol at room temperature for at least 8 hours.

5. The concentrating column of claim 1, wherein cleansing of the macroporous adsorbent resin of high, medium or non-polarity is carried out by washing with deionized water.

6. The concentrating column of claim 2, wherein the dynamic on-column treatment with a mixture of NH$_4$OH-HAC-pyridin-(2-azo-4-)resorcin comprises the steps of:
packing the swollen and cleaned macroporous adsorbent resin of high, medium or non-polarity into column,
pumping the formulated mixture of 3 mol/L NH$_4$OH-1 mol/L HAC-3.0~6.0×10$^{-4}$ mol/L pyridin-(2-azo-4-)resorcin undiluted or diluted 2–4 times with deionized water into the concentrating column until the effluent turns from colorless to orange, and
washing the concentrating column with deionized water through the column until the effluent turns from orange to colorless.

7. The concentrating column of claim 2, wherein the dynamic on-column treatment with a mixture of Na$_2$HPO$_4$-pyridin-(2-azo-4-)resorcin comprises the steps of:
packing the swollen and cleaned macroporous adsorbent resin of high, medium or non-polarity into column,
pumping the formulated mixture of 0.5 mol/L Na$^2$HPO$_4$-1.0~2.0×10$^{-4}$ mol/L pyridin-(2-azo-4-)resorcin into the concentrating column until the effluent turns from colorless to orange red, and
washing the concentrating column with deionized water through the column until the effluent turns from orange red to colorless.

8. The concentrating column of claim 3, wherein the static immersion treatment with a mixture of NH$_4$OH-HAC-pyridin-(2-azo-4-) resorcin comprises the steps of:
immersing the swollen and cleaned macroporous adsorbent resin of high, medium or non-polarity in the formulated mixture of 3 mol/L NH$_4$OH-1 mol/L HAC-3.0~6.0×10$^{-4}$ mol/L pyridin-(2-azo-4-) resorcin under room temperature for at least 30 minutes, and
washing it with deionized water until the washing fluid turns colorless.

9. The concentrating column of claim 3, wherein the static immersion treatment with a mixture of Na$_2$HPO$_4$-pyridin-(2-azo-4-)resorcin comprises the steps of:
immersing the swollen and cleaned macroporous adsorbent resin of high, medium or non-polarity in the formulated mixture of 0.5 mol/L Na$^2$HPO$_4$-1.0~2.0×10$^{-4}$ mol/L pyridin-(2-azo-4-)resorcin under room temperature for at least 30 minutes, and
washing it with deionized water until the washing fluid turns colorless.

10. A sample processing device useful for elemental analysis of trace metals comprising a concentrating column, a low pressure pump, a switch valve, a washing fluid container, a sample container, a desorption fluid container, and additionally a six-way automatic sampling valve and a transporting pump, wherein:
the inlet of the transporting pump is connected to the desorption fluid container via pipe fittings,
the outlet of transporting pump is connected to one fluid inlet of the six-way valve via pipe fittings,
the outlet of the low pressure pump is connected to one fluid inlet of the six-way automatic sampling valve via pipe fittings,
the inlet of the low pressure pump is connected to the outlet of the switch valve via pipe fittings,
the inlets of the switch valve are connected to the sample container and the washing fluid container respectively via pipe fittings,
the concentrating column comprises a column body, filtration membranes fixed at the fluid inlet end and the outlet end of the column body, and column packing packed inside the column body, wherein the column packing is prepared from the swollen and cleaned macroporous adsorbent resin of high, medium or non-polarity treated with a mixture of 3 mol/L $NH_4OH$-1 mol/L HAC-3.0~6.0×$10^{-4}$ mol/L pyridin-(2-azo-4-)resorcin or a mixture of 0.5 mol/L $Na_2HPO_4$-1.0~2.0×$10^{-4}$ mol/L pyridin-(2-azo-4-)resorcin, and the fluid inlet and outlet of the concentrating column are connected via pipe fittings to fluid outlet and inlet of the six-way automatic sampling valve respectively.

11. The sample processing device of claim 10, wherein the swollen and cleaned macroporous adsorbent resin of high, medium or non-polarity is treated by dynamic on-column treatment.

12. The sample processing device of claim 10, wherein the swollen and cleaned macroporous adsorbent resin of high, medium or non-polarity is treated by static immersion treatment.

13. A sample processing device useful for elemental analysis of trace metals comprising a concentrating column, a low pressure pump, a switch valve, a washing fluid container, a sample container and a desorption fluid container, with the outlet of the low pressure pump being connected to the fluid inlet of the concentrating column via pipe fittings, the inlet of the low pressure pump being connected to the outlet of the switch valve via pipe fittings, and the inlets of the switch valve being connected via pipe fittings to the sample container, the washing fluid container and the desorption fluid container respectively, wherein:

the concentrating column comprises column body, filtration membranes fixed at the fluid inlet end and the outlet end of the column body, and the column packing packed inside the column body, wherein the column packing is prepared from the swollen and cleaned macroporous adsorbent resin of high, medium or non-polarity treated with a mixture of 3 mol/L $NH_4OH$-1 mol/L HAC-3.0~6.0×$10^{-4}$ mol/L pyridin-(2-azo-4-)resorcin or a mixture of 0.5 mol/L $Na_2HPO_4$-1.0~2.0×$10^{-4}$ mol/L pyridin-(2-azo-4-)resorcin.

14. The sample processing device of claim 13, wherein the swollen and cleaned macroporous adsorbent resin of high, medium or non-polarity is treated by dynamic on-column treatment.

15. The sample processing device of claim 13, wherein the swollen and cleaned macroporous adsorbent resin of high, medium or non-polarity is treated by static immersion treatment.

* * * * *